United States Patent [19]

Van Den Besselaar

[11] Patent Number: 5,689,544
[45] Date of Patent: Nov. 18, 1997

[54] X-RAY EXAMINATION APPARATUS COMPRISING A BEAM DIAPHRAGM

[75] Inventor: Fransiscus J. M. Van Den Besselaar, Eindhoven, Netherlands

[73] Assignee: U.S. Philips Corporation, New York, N.Y.

[21] Appl. No.: 558,064

[22] Filed: Nov. 13, 1995

[30] Foreign Application Priority Data

Nov. 21, 1994 [EP] European Pat. Off. ............ 94203375

[51] Int. Cl.⁶ .................................................. A61B 6/06
[52] U.S. Cl. .................................... 378/150; 378/152
[58] Field of Search ............................ 378/150, 152, 378/153

[56] References Cited

U.S. PATENT DOCUMENTS

| | | | |
|---|---|---|---|
| 4,752,947 | 6/1988 | Telorack | 378/152 |
| 5,086,444 | 2/1992 | Bartmann | 378/152 |
| 5,260,984 | 11/1993 | Horbaschek | 378/150 X |
| 5,287,396 | 2/1994 | Stegehuis | 378/150 X |

*Primary Examiner*—David P. Porta
*Attorney, Agent, or Firm*—Jack D. Slobod

[57] ABSTRACT

An X-ray examination apparatus includes a beam diaphragm (3) with an X-ray absorbing shutter (4, 31, 32) which is arranged between the X-ray source (1) and the X-ray detector (9) in order to intercept parts of the X-ray beam (2), thus forming a limited X-ray beam (7). The shutter (4, 31, 32) can be displaced according to different degrees of freedom by different rotations of control rings (21, 22, 41, 42, 47, 48) whereto the shutter (4, 31, 32) is coupled. Because the shutter (4, 31, 32) can be moved to practically any desired position within the X-ray beam (2), the beam diaphragm (3) can shape the cross-section of the limited X-ray beam (7) in such a manner that essentially only a part (5) of a patient (6) to be examined is exposed to X-rays.

8 Claims, 2 Drawing Sheets

X-RAY EXAMINATION APPARATUS COMPRISING A BEAM DIAPHRAGM

BACKGROUND OF THE INVENTION

1. Field of the Invention

The invention relates to an X-ray examination apparatus, comprising a beam diaphragm with a shutter comprising an adjusting member for varying a shutter aperture.

2. Description of the Related Art

An X-ray examination apparatus of this kind is known from U.S. Pat. No. 5,086,444.

The known X-ray examination apparatus comprises an X-ray source for emitting an X-ray beam whereto an object, for example a patient to be examined, placed between the X-ray source and an X-ray detector is exposed. An X-ray image is formed on the X-ray detector because of differences in the X-ray absorption within the patient. In order to shield parts of the patient from the X-ray beam, between the X-ray source and the patient there is arranged a beam diaphragm with the X-ray absorbing shutter which can be moved into and out of the X-ray beam in order to adjust the shutter aperture so as to intercept parts of the X-ray beam, if desired. For example, during an examination of the heart and the coronary vessels of a patient the shutter is adjusted to shield the surrounding lung tissue as much as possible from the X-rays and to expose exclusively the region of the heart to the X-ray beam.

In the known X-ray examination apparatus the shutter is provided with a pin and is controlled by an adjusting member which comprises a single control ring provided with a groove of permanent shape in which the pin engages. The shutter is moved by rotating the control ring so that the groove takes along the pin. The permanent shape of the groove determines the motion of the shutter and it is not possible to make the shutter perform different motions independently of one another in order to vary the shutter aperture, for example sliding into and out of the X-ray beam and rotation. Because the possibilities for motion of the known shutter are limited, the cross-section of the X-ray beam can only be conditionally matched accurately with a region of the patient to be examined. Because the known shutter often does not allow for a limited X-ray beam to be formed which has a cross-section which accurately matches a region of a patient to be examined, notably when said region is of complex shape, parts of the patient outside the region to be examined will be unnecessarily exposed to X-rays, so that the patient is exposed to an X-ray dose which is higher than required for the formation of a high-quality X-ray image. Moreover, if the X-ray absorption of such parts is low, overexposed areas occur in the X-ray image, so that the diagnostic quality of the X-ray image is degraded.

SUMMARY OF THE INVENTION

It is an object of the invention to provide an X-ray examination apparatus which comprises a beam diaphragm which, in comparison with the known X-ray apparatus, offers more possibilities for forming a limited X-ray beam of a cross-section which accurately corresponds to a region to be irradiated.

To achieve this, an X-ray examination apparatus in accordance with the invention is characterized in that the shutter is radially slidable and rotatable in a plane transversely of a central axis of the beam diaphragm by mutually independent rotation of two control rings forming part of the adjusting member.

Rotation of the control rings enables the shutter to be moved to practically any desired position in the X-ray beam in a number of different, independent manners, the shutter aperture thus being adjusted so as to control the cross-section of the limited X-ray beam in such a manner that essentially only a region of the object to be examined is exposed to the X-ray beam. Different relative rotations of two control rings coupled to the shutter are independently transferred to different modes of movement of the shutter, such as sliding motions and rotations over different distances or angles.

When the shutter is made of a material having a high X-ray absorptivity, for example a lead plate having a thickness of a few millimeters, a part of the X-ray beam which is incident on the shutter is stopped by the shutter so that it cannot reach the patient. It is also possible to construct the shutter using a material, for example a copper plate having a thickness of approximately one millimeter, whose X-ray absorptivity is less than required to intercept the X-rays completely. Such a shutter attenuates the X-rays and operates as an X-ray filter to avoid overexposure of parts in the X-ray image which correspond to regions of low X-ray absorptivity within the patient.

Because the control rings have a small thickness and are coupled to the shutter by means of a limited number of components, they are particularly suitable for a compact beam diaphragm.

A preferred embodiment of an X-ray examination apparatus in accordance with the invention is characterized in that the shutter is rotatable by rotation of said two control rings in the same direction.

The rotation in the same direction of the two control rings coupled to the shutter is transferred to rotation of the shutter in a plane approximately transversely of the X-ray beam. This rotation of the shutter is independent of other possible movement modes of the shutter. As a result, the shutter can be moved so as to occupy substantially any desired azimuthal orientation in the X-ray beam in order to achieve accurate matching between the cross-section of the limited X-ray beam and the region to be irradiated.

The shutter is preferably shaped as a rectangular, flat plate and can be mounted in the X-ray examination apparatus in such a manner that the axis of rotation of the shutter is coincident with the central ray of the X-ray beam. Rotation of the control rings then enables movement of the shutter in the X-ray beam in order to intercept a more or less half-moon part of the approximately circular cross-section of the X-ray beam passing through the beam diaphragm. This approximately half-moon part is limited by a straight edge of the shutter and a circular arc of the circumference of the approximately circular cross-section of the X-ray beam. Practically any orientation of the half-moon part can be realized by rotation of the shutter by means of the control rings.

Alternatively, the shutter can be mounted in the X-ray examination apparatus in such a manner that the axis of rotation of the shutter does not coincide with the central ray of the X-ray beam. Rotation of the control rings then enables movement of the shutter in the X-ray beam in order to intercept a more or less sector-shaped part of the X-ray beam passing through the beam diaphragm. This sector-shaped part is limited by a corner of the shutter and a circular arc of the circumference of the approximately circular cross-section. The size of the more or less sector-shaped part is controlled on the basis of the angle wherethrough the control rings are rotated together. Thus, a large variety of sizes and orientations of the sector-shaped part of the X-ray beam to be intercepted by the shutter can be realized by adjustment of the shutter.

A further preferred embodiment of an X-ray examination apparatus in accordance with the invention is characterized in that the shutter is slidable by rotation of said two control rings in opposite directions.

The rotation in opposite directions of the two control rings coupled to the shutter is transferred to sliding of the shutter in a direction approximately towards the center of the X-ray beam. This sliding of the shutter is independent of other feasible movement modes of the shutter.

By sliding the shutter transversely into the X-ray beam, the shutter will intercept a more or less half-moon part of the desired dimensions from the approximately circular cross-section of the X-ray beam. The degree whereto the control rings are rotated in opposite directions determines the size of the more or less half-moon part.

A further preferred embodiment of an X-ray examination apparatus in accordance with the invention is characterized in that the beam diaphragm comprises a plurality of similar shutters which are arranged consecutively in the direction of the X-ray beam.

Each of the shutters can be moved into and out of the X-ray beam from different directions by rotation and/or sliding of the control rings. When the respective shutters are suitably arranged, the patient can be exposed to an X-ray beam of complex cross-section, for example a polygon whose sides and comers can be arbitrarily adjusted by the positioning of the shutters. As a result, the cross-section can be accurately adapted in respect of shape and dimensions to a part of a patient to be examined who is irradiated by the X-ray beam. The more shutters are provided so as to slide into the X-ray beam from different directions, the larger the maximum number of arbitrarily selectable sides will be of the polygon which limits the cross-section of the X-ray beam incident on the patient. Therefore, the use of a beam diaphragm comprising a plurality of shutters enables more complex shapes of the cross-section of the X-ray beam to be realized and accurate matching between the cross-section and the region to be examined is more often possible.

These and other aspects of the invention will be apparent from and elucidated with reference to the accompanying drawings and the embodiments described hereinafter.

DETAILED DESCRIPTION OF THE PREFERRED EMBODIMENTS

Figure 1:
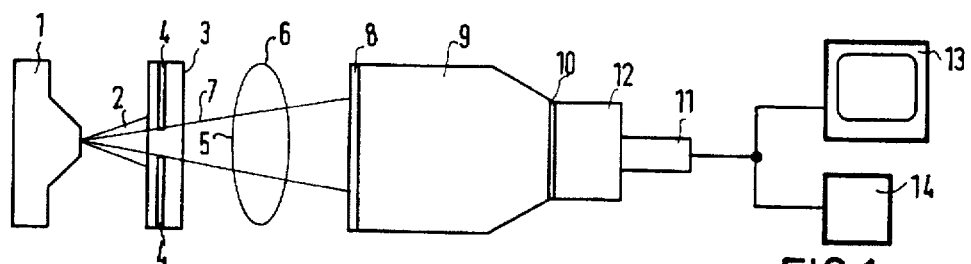
FIG. 1 shows diagrammatically an embodiment of an X-ray examination apparatus comprising a beam diaphragm in accordance with the invention.

FIG. 1 shows diagrammatically an X-ray examination apparatus comprising a beam diaphragm in accordance with the invention. An X-ray source 1 emits an X-ray beam 2 which is limited by a beam diaphragm 3 comprising a shutter 4. A part 5 of an object 6, for example of a patient 6 to be examined, is exposed to the limited X-ray beam 7 so that as a result of differences in absorption within the patient an X-ray image is formed as a shadow image on an entrance screen 8 of X-ray image intensifier 9; this image is converted into a light image on an exit window 10. The light image on the exit window is picked up by a video camera 11 which is coupled to the exit window 10 by means of an optical transmission 12, for example a system comprising one or more lenses. The video camera 11 derives an electronic signal from the light image, which electronic image signal is applied to a monitor 13 in order to reproduce the image information; the electronic image signal can also be applied to an image processing unit 14 for further processing of the image information.

Figure 2:
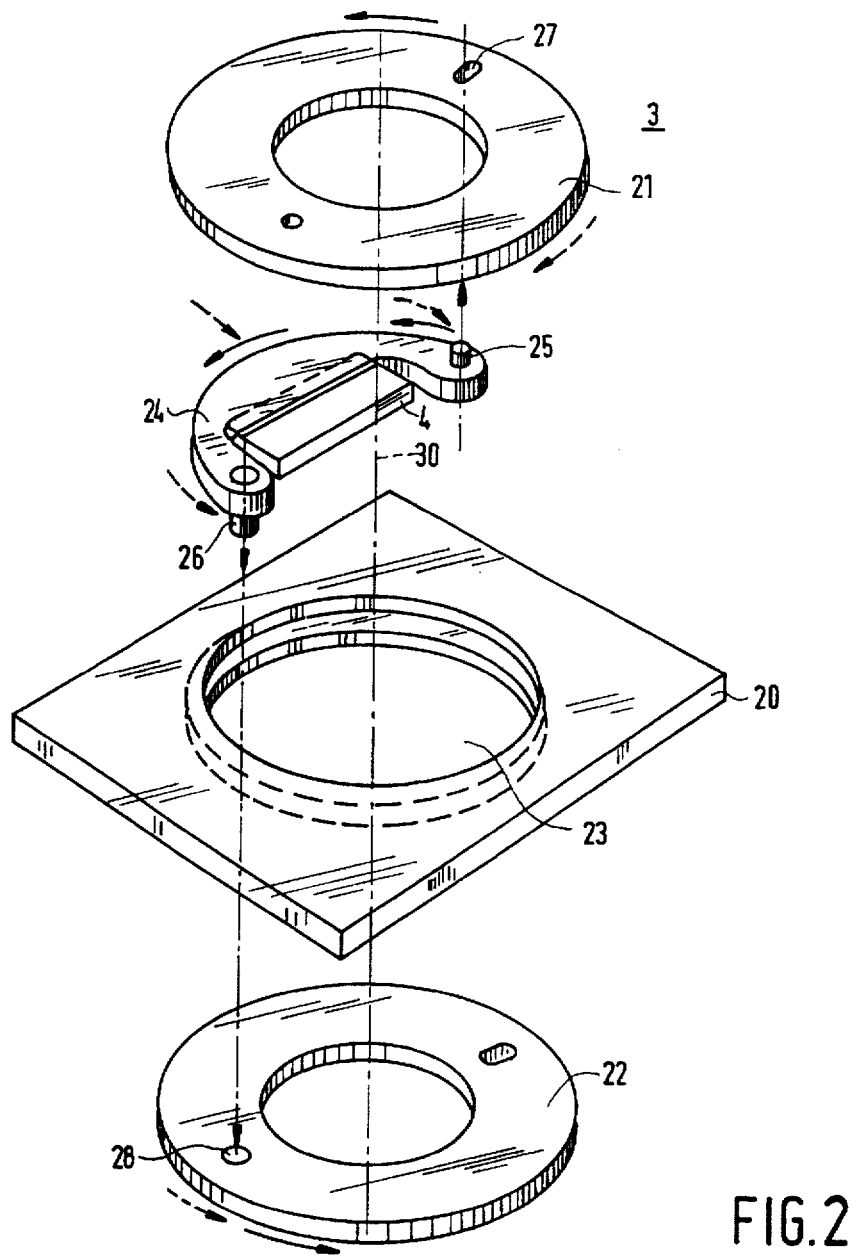
FIG. 2 is an exploded view of a beam diaphragm of an embodiment of an X-ray examination apparatus in accordance with the invention.

FIG. 2 is an exploded view of a beam diaphragm 3 of an embodiment of an X-ray examination apparatus in accordance with the invention. The adjusting member for the shutter comprises a first control ring 21 and a second control ring 22 which are arranged one to each side of a carrier plate 20. The control rings are rotatably journalled relative to the carrier plate. The carrier plate 20 comprises a round shutter aperture 23 for the passage of the X-ray beam. The shutter aperture can be partly covered by the control rings, depending on the width of the control rings; the size of the shutter aperture is then determined by the openings in the control rings. The shutter 4, having a flat rectangular shape, is mounted on a frame 24 provided with two pins 25 and 26. The first pin 25 engages a slot 27 in the first control ring 21 and the second pin engages a hole 28 in the second control ring 22. The length of the slot 27 amounts to a few times its width and the longitudinal direction of the slot 27 is oriented radially relative to the axis of the first control ring. This transmission by means of pins engaging openings requires the use of a limited number of simple components only.

The shutter 4 is moved into and out of the region of passage of the X-ray beam by rotation of the control rings 21 and 22. The control rings are driven by means of actuators; to this end, each of the control rings is provided, for example with a toothed portion which is engaged by a gearwheel driven by an actuator. Each of the control rings may be coupled to a respective actuator, but it is also possible to couple a plurality of control rings to one and the same actuator. The control rings cooperate with the frame for displacement of the shutter in various, independent manners. When the control rings are rotated in the same directions at the same angular speeds, for example both control rings counter-clockwise as denoted by the solid arrows, the control rings 21 and 22 rotate the frame with the shutter counter-clockwise. The control rings 21 and 22 are mounted, for example in such a manner that their axes are coincident with the central axis 30 of the beam diaphragm, so that the shutter is rotatable about the central axis of the beam diaphragm with which the central ray of the X-ray beam emitted by the X-ray source is coincident, and so that by rotation of the shutter a more or less half-moon intercepted part of the approximately circular cross-section of the X-ray beam is rotated about the central axis 30. The control rings 21 and 22 can alternatively be mounted so that their axes are mutually coincident and shifted parallel to the central axis, so that the shutter 4 is rotatable about an axis which is not coincident with the central axis. Upon rotation of the shutter about this axis it is moved in and out of the X-ray beam, thus intercepting a more or less sector-shaped part of the approximately circular cross-section of the X-ray beam, the size of which part is controlled on the basis of the angle wherethrough the control rings 21 and 22 are rotated.

When the control rings are rotated in opposite directions at the same angular speeds, for example the first control ring 21 counter-clockwise and the second control ring 22 clockwise as indicated by the dashed arrows, the control rings 21 and 22 slide the frame with the shutter radially (relative to the central axis 30), into the X-ray beam; the shutter is slid out of the X-ray beam by rotating the control rings in the reverse directions, the pin 25 then being displaced a distance through the slot 27. The size of a more or less half-moon part of the X-ray beam intercepted by the shutter is varied by moving the shutter into the X-ray beam to a desired extent by rotating the control rings in opposite directions.

If the control rings are rotated about their axes at angular speeds which are not the same, combined rotation and sliding of the shutter takes place.

Figure 3:
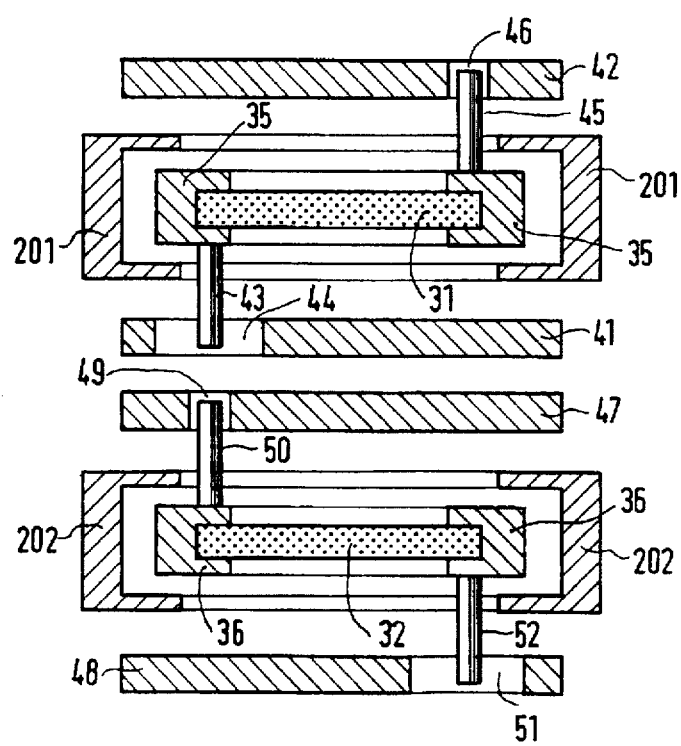
FIGS. 3 and 4 are a side elevation and a plan view, respectively, of a beam diaphragm of a further embodiment of an X-ray examination apparatus in accordance with the invention.

FIG. 3 is a side elevation of a beam diaphragm of a further embodiment of an X-ray examination apparatus in accordance with the invention. The first shutter 31 in a first carrier plate 201 and the second shutter 32 in a second carrier plate 202 are arranged one behind the other. The first shutter is mounted on a frame 35 which is coupled, by way of pins 43 and 45, to a first pair of control rings consisting of the control ring 41 and the control ring 42. The pin 43 engages a slot 44 in the control ring 41 and the pin 45 engages a hole 46 in the control ring 42. The second shutter 32, provided in the second carrier plate 202, is mounted on a frame 36 which is coupled to a second pair of control rings 47 and 48 by way of pins 50 and 52 which engage a hole 49 and a slot 51, respectively, in the control ting 47 and the control ring 48, respectively. Upon rotation of the control rings their movement is transferred to the pins 43, 45, 50 and 52 which take along the frames 35 and 36 with the shutters 31 and 32.

Figure 4:
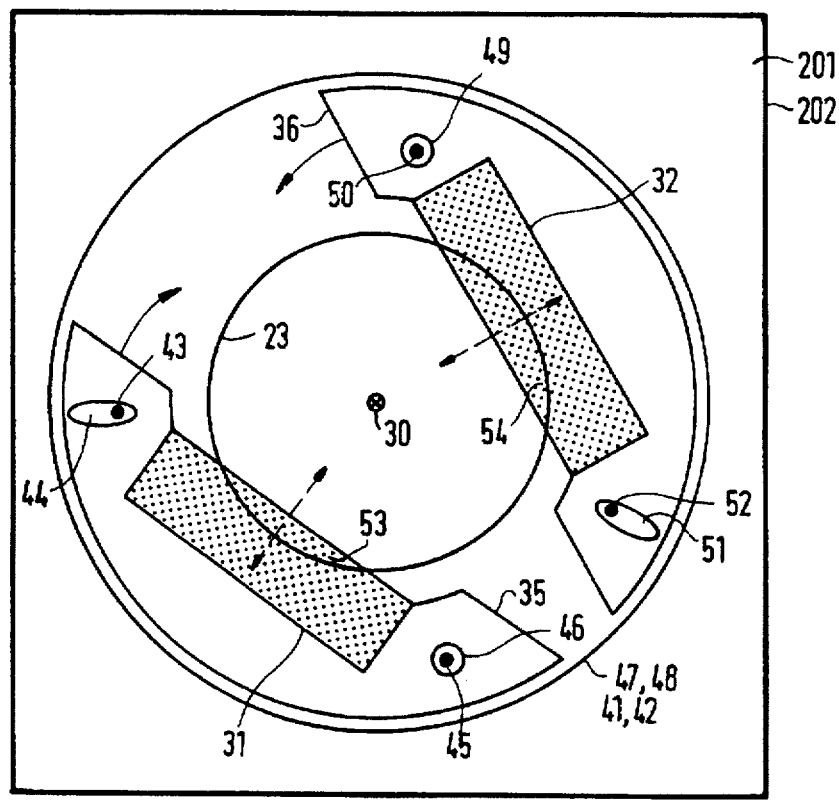

FIG. 4 is a plan view of the beam diaphragm of FIG. 3, forming part of an X-ray examination apparatus in accordance with the invention. A circular aperture 23 in the carrier plate 20 for the passage of the X-ray beam 2 can be fully or partly closed by means of the X-ray absorbing shutters 31 and 32 which can be moved into and out of the X-ray beam by rotation of pairs of control rings 41, 42 and 47, 48 in order to intercept, if desired, a part of the cross-section of the X-ray beam. The directions in which the shutters can be moved in the drawing are denoted by the solid arrows which indicate rotation of the shutter about the axis 30 and by the dashed arrows which indicate the sliding of the shutter into and out of the X-ray beam. The drawing also shows the approximately half-moon parts 53 and 54 of the cross-section of the X-ray beam in which the X-rays are intercepted by the shutter. The shutters can also be coupled to the respective central rings by providing the shutters, or the carrier frames on which the shutters are mounted, with a hole or a slot and by providing the central rings with a pin which engages the hole or slot in the relevant shutter or carrier frame.

I claim:

1. An X-ray examination apparatus, comprising a beam diaphragm with a plurality of shutters and adjusting means coupled to the pair of shutters for varying a shutter aperture of the beam diaphragm comprising a plurality of control rings, said adjusting means being configured such that the plurality of shutters are mutually independently radially slidable and rotatable transversely of the central axis of the beam diaphragm and each of the shutters is adjusted by mutually independent rotation of a different associated two of said plurality of control rings, said mutually independent rotation of each different associated two of said plurality of control rings adjusting one and only one of said shutters.

2. An X-ray examination apparatus as claimed in claim 1, characterized in that the plurality of shutters which are arranged consecutively in the direction of a central axis of the beam diaphragm.

3. An X-ray examination apparatus as claimed in claim 1, characterized in that each shutter is slidable by rotation of its associated two control rings in opposite directions.

4. An X-ray examination apparatus as claimed in claim 3, characterized in that the plurality of shutters which are arranged consecutively in the direction of a central axis of the beam diaphragm.

5. An X-ray examination apparatus as claimed in claim 1, characterized in that each shutter is rotatable by rotation of its associated two control rings in the same direction.

6. An X-ray examination apparatus as claimed in claim 5, characterized in that each shutter is slidable by rotation of its associated two control rings in opposite directions.

7. An X-ray examination apparatus as claimed in claim 6, characterized in that the plurality of shutters which are arranged consecutively in the direction of a central axis of the beam diaphragm.

8. An X-ray examination apparatus as claimed in claim 5, characterized in that the plurality of shutters which are arranged consecutively in the direction of a central axis of the beam diaphragm.

* * * * *